United States Patent [19]

Eto et al.

[11] Patent Number: 5,200,395

[45] Date of Patent: Apr. 6, 1993

[54] PHARMACEUTICAL COMPOSITION OF BUF-5 FOR TREATING ANEMIA

[75] Inventors: Yuzuru Eto; Naoto Koyama; Daisuke Ejima; Masayo Washitake; Hiroshiro Shibai, all of Kawasaki, Japan

[73] Assignee: Ajinomoto Company, Inc., Tokyo, Japan

[21] Appl. No.: 784,685

[22] Filed: Oct. 29, 1991

Related U.S. Application Data

[63] Continuation of Ser. No. 617,259, Nov. 23, 1990, abandoned, which is a continuation of Ser. No. 423,875, Oct. 18, 1989, abandoned.

[30] Foreign Application Priority Data

Oct. 18, 1988 [JP] Japan .................................. 63-262321
Oct. 18, 1988 [JP] Japan .................................. 63-262322
Oct. 18, 1988 [JP] Japan .................................. 63-262323

[51] Int. Cl.⁵ .............................................. A61K 37/02
[52] U.S. Cl. ........................................ 514/12; 514/2; 530/350
[58] Field of Search ....................... 514/12, 2; 530/350

[56] References Cited

U.S. PATENT DOCUMENTS 4,740,587  4/1988  Ling et al. ........................... 530/328

OTHER PUBLICATIONS

Mason et al. Nature 318, pp. 659–663 (1985).
Ling et al. Nature 321, pp. 779–792 (1986).

*Primary Examiner*—Robert J. Hill, Jr.
*Assistant Examiner*—Shelly J. Guest
*Attorney, Agent, or Firm*—Oblon, Spivak, McClelland, Maier & Neustadt

[57] ABSTRACT

The polypeptides BUF-4 and BUF-5 may be used to treat osteoporosis, cancer, and anemia, and pharmaceutical compositions containing BUF-4 and/or BUF-5 are disclosed.

1 Claim, 2 Drawing Sheets

```
 1                                      10
Gly Leu Glu Cys Asp Gly Lys Val Asn Ile
11                                      20
Cys Cys Lys Lys Gln Phe Phe Val Ser Phe
21                                      30
Lys Asp Ile Gly Trp Asn Asp Trp Ile Ile
31                                      40
Ala Pro Ser Gly Tyr His Ala Asn Tyr Cys
41                                      50
Glu Gly Glu Cys Pro Ser His Ile Ala Gly
51                                      60
Thr Ser Gly Ser Ser Leu Ser Phe His Ser
61                                      70
Thr Val Ile Asn His Tyr Arg Met Arg Gly
71                                      80
His Ser Pro Phe Ala Asn Leu Lys Ser Cys
81                                      90
Cys Val Pro Thr Lys Leu Arg Pro Met Ser
91                                      100
Met Leu Tyr Tyr Asp Asp Gly Gln Asn Ile
101                                     110
Ile Lys Lys Asp Ile Gln Asn Met Ile Val
111
Glu Glu Cys Gly Cys Ser
```

| | |
|---|---|
| 1 | 10 |

Gly Leu Glu Cys Asp Gly Lys Val Asn Ile
11                                    20
Cys Cys Lys Lys Gln Phe Phe Val Ser Phe
21                                    30
Lys Asp Ile Gly Trp Asn Asp Trp Ile Ile
31                                    40
Ala Pro Ser Gly Tyr His Ala Asn Tyr Cys
41                                    50
Glu Gly Glu Cys Pro Ser His Ile Ala Gly
51                                    60
Thr Ser Gly Ser Ser Leu Ser Phe His Ser
61                                    70
Thr Val Ile Asn His Tyr Arg Met Arg Gly
71                                    80
His Ser Pro Phe Ala Asn Leu Lys Ser Cys
81                                    90
Cys Val Pro Thr Lys Leu Arg Pro Met Ser
91                                   100
Met Leu Tyr Tyr Asp Asp Gly Gln Asn Ile
101                                  110
Ile Lys Lys Asp Ile Gln Asn Met Ile Val
111
Glu Glu Cys Gly Cys Ser

*FIG. 1*

```
  1                                          10
Gly Leu Glu Cys Asp Gly Arg Thr Asn Leu
 11                                          20
Cys Cys Arg Gln Gln Phe Phe Ile Asp Phe
 21                                          30
Arg Leu Ile Gly Trp Asn Asp Trp Ile Ile
 31                                          40
Ala Pro Thr Gly Tyr Tyr Gly Asn Tyr Cys
 41                                          50
Glu Gly Ser Cys Pro Ala Tyr Leu Ala Gly
 51                                          60
Val Pro Gly Ser Ala Ser Ser Phe His Thr
 61                                          70
Ala Val Val Asn Gln Tyr Arg Met Arg Gly
 71                                          80
Leu Asn Pro Gly Thr Val Asn Ser Cys Cys
 81                                          90
Ile Pro Thr Lys Leu Ser Thr Met Ser Met
 91                                         100
Leu Tyr Phe Asp Asp Glu Tyr Asn Ile Val
101                                         110
Lys Arg Asp Val Pro Asn Met Ile Val Glu
111
Glu Cys Gly Cys Ala
```

*FIG. 2*

PHARMACEUTICAL COMPOSITION OF BUF-5 FOR TREATING ANEMIA

This application is a continuation of application Ser. No. 07/617,259, filed Nov. 23, 1990, which was a continuation of application Ser. No. 07/423,875, filed on Oct. 18, 1989, both now abandoned.

BACKGROUND OF THE INVENTION

FIELD OF THE INVENTION

The present invention relates to pharmaceutical compositions containing as an effective ingredient, at least one substance selected from the polypeptides BUF-4 and BUF-5 (hereafter referred to as BUF-4 and BUF-5), more particularly, to pharmaceutical compositions containing, as an effective ingredient, at least one substance selected from BUF-4 and BUF-5 which exhibit therapeutic effects on any of osteoporosis, anemia, and cancer and methods of treating osteoporosis, anemia, and cancer by administering of BUF-4 or BUF-5.

DISCUSSION OF THE BACKGROUND

With the increased population of aged people, the number of patients with osteoporosis has also recently increased, resulting in a serious social problem. The number of patients suffering from osteoporosis in Japan, is currently estimated to be approximately 4 million people. Osteoporosis is a disease which results in a decrease in the amount of bone or skeletal tissue atrophy. The disease is extremely dangerous in that as the amount of bone decreases, the trabecula becomes narrow which causes bones to become fragile, and as the result, the vertebra, femur, cervical vertebra, etc. are broken.

The disease is roughly classified into two types: (1) post-menopausal osteoporosis found in women after menopause and (2) senile osteoporosis found in aged people irrespective of sex.

As drugs for treating osteoporosis, calcitonin which prevents osteolysis, female hormones (administered especially to post-menopausal women), activated vitamin $D_3$, anabolic steroid hormones, etc. have been hitherto used.

However, these therapeutic agents are unsuccessful for drastic treatment which not only checks the decrease in the amount of bone but also increases the amount of bone. In addition, the therapeutic agents raise the question of side effects. For example, when vitamin $D_3$ is used, hyper-calcinurea appears. As such, all of these therapeutic agents cause problems in that several side effects are involved.

Therefore, it is desired to develop drugs for treating osteoporosis capable of checking the decrease in an amount of bone and actually increasing the amount of bone and which cause minimal side effects.

As drugs for treating anemia, different drugs are used depending upon the cause of the anemia. In general, iron agents are used for iron deficiency anemia, vitamin $B_{12}$ or folic acid is used for pernicious anemia and adrenal cortical hormones such as corticoid, etc. are used for aplastic anemia and hemolytic anemia. Among them, steroid hormones are shown to have an erythropoietic stimulating effect and are effective therapeutic agents. However, the most serious problem is their potent side effect, and there is a problem when they are administered over long periods of time.

In recent years, attention has been paid to erythropoietin as a vital substance that participates in formation of red blood cells and improves anemia. Erythropoietin is a glycoprotein having a molecular weight of 45,000, which is produced in the kidney and is present in the -globulin fraction. Erythropoietin is defined to be a humoral regulation factor that acts on hematopoietic stem cells and stimulates differentiation into and formation of erythroblasts. Erythopoietin is expected to be a new drug for treating anemia. However, its source material is human urine and the content is extremely small so that it is difficult to supply erythropoietin in large quantities. On the other hand, its production by genetic recombination has also been investigated but is still under way.

Accordingly, it is also desired to develop drugs for treating anemia having minimal side effects.

On the other hand, for treatment of cancer, chemotherapy using chemical substances has been performed heretofore, in addition to surgical therapy and radiotherapy. The chemotherapy which has been performed heretofore has been developed mainly in accord with the basic principle of directly killing cancer cells by the use of cytotoxic substances. In this manner, to research and develop an anticancer agent, attention is directed to the abnormal growth of cancer cells. Such anticancer agents inhibit DNA replication of cells, e.g., mitomycin C or nitrogen mustard, or inhibit nucleic acid metabolism, e.g., methotrexate or 5-fluorouracil. Most of these drugs are known to exhibit marked effects on cancer cells having active cell division such as leukemia cells.

However, it is known that these drugs produce side effects. In particular, these drugs also strongly inhibit normal myeloid cells which have a rapid metabolism turnover equally to or more than cancer cells. It is thus the actual situation that, in light of the side effects such as anemia, leukopenia, etc. caused by the inhibition, these drugs must be administered in a dose between the effective dose and the dose causing toxicity, such that the dose is not fatal to the patient.

Therefore, in the case of anticancer agents, it is also desired to develop drugs which have a potent anticancer effect with minimal side effects, as in the case of drugs for treating anemia and osteoporosis described above.

SUMMARY OF THE INVENTION

Accordingly, it is an object of the present invention to provide pharmaceutical compositions which contain substances which cause minimal side effects and are effective for treating anemia, osteoporosis, or cancer.

It is another object of the present invention to provide a method for treating osteoporosis.

It is another object of the present invention to provide a method for treating anemia.

It is another object of the present invention to provide a method for treating cancer.

These and other objects, which will become apparent during the course of the following detailed description, have been achieved by the inventors' discovery that the polypeptides BUF-4 and BUF-5 may be used for the effective treatment of (1) anemia, (2) cancer, and (3) osteoporosis.

That is, the pharmaceutical compositions of the present invention are characterized as containing, as an effective ingredient, at least one substance selected from the polypeptides BUF-4 and BUF-5.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows an amino acid sequence of monomer A.

FIG. 2 shows an amino acid sequence of monomer B.

DETAILED DESCRIPTION OF THE PREFERRED EMBODIMENTS

Thus, one aspect of the present invention relates to pharmaceutical compositions which contain at least one of BUF-4 and BUF-5. These compounds are characterized as follows:

(1) Physicochemical properties of BUF-4

| | |
|---|---|
| (a) Structure: | heterodimer of monomer A (cf. FIG. 1) and monomer B (cf. FIG. 2) |
| (b) Molecular weight: | both monomer A and monomer B: 16 ± 1 kd (kilodalton) as monomer (in the presence of 1.0% mercaptoethanol, SDS-electrophoresis) 25 ± 1 kd as heterodimer (in the absence of 1.0% mercaptoethanol, SDS-electrophoresis) |
| (c) Isoelectric point: | pI 7.3 ± 0.5 (isoelectric point electrophoresis) |
| (d) pH stability: | stable in a pH range of from 2.0 to 10.0 |
| (e) Heat stability: | It is stable to heating at 65° C. for 60 minutes. |
| (f) Stability in organic solvent: | It is stable in lower alcohols and acetonitrile. |
| (g) Resistance to protease: | It is completely inactivated by treatment with pronase. |
| (h) Amino acid sequence: | Amino acid sequences of monomer A and monomer B are shown in FIG. 1 and FIG. 2, respectively. |

(2) Physicochemical properties of BUF-5

| | |
|---|---|
| (a) Structure: | homodimer of monomer B |
| (b) Molecular weight: | 16 ± 1 kd as monomer (in the presence of 1.0% mercaptoethanol, SDS-electrophoresis) 25 ± 1 kd as homodimer (in the absence of mercaptoethanol, SDS-electrophoresis) |
| (c) Isoelectric point: | pI 7.3 ± 0.5 (isoelectric point electrophoresis) |
| (d) pH stability: | stable in a pH range of from 2.0 to 10.0 |
| (e) Heat stability: | It is stable to heating at 65° C. for 60 minutes. |
| (f) Stability in organic solvent: | It is stable in lower alcohols and acetonitrile. |
| (g) Resistance to protease: | It is completely inactivated by treatment with pronase. |
| (h) Amino acid sequence: | Amino acid sequence of monomer B is shown in FIG. 2. |

The BUF-4 and BUF-5 of the present invention also include any substances so long as they have the same activity even if they do not have quite the same amino acid sequences as shown in FIGS. 1 and 2.

That is, the BUF-4 and BUF-5 of the present invention also include substances having a structure in which one or more amino acids in the amino acid sequence shown in FIG. 1 or FIG. 2 are replaced with other amino acids, a substance having a structure in which one or more amino acids are added to the N-terminus or C-terminus of the amino acid sequence shown in FIG. 1 or FIG. 2, and further a substance having a structure wherein one or more amino acids from the N-terminus or C-terminus in the amino acid sequence shown in FIG. 1 or FIG. 2 are deleted or continued. It has already been reported that BUF-4 has an activity of secreting follicle stimulating hormone (Vale, W., River, J., Vaughan, J., McClintock, R., Corrigan, A., Woo, W., Karr, D. and Spiess, J., Nature, Vol. 321, 776–777 (1986)).

BUF-4 is also called activin, but the term BUF-4 is used in the present invention.

On the other hand, BUF-5 is disclosed in Japanese Patent Application Laid-Open No. 119679/1988.

As described above, it is already known that BUF-4 and BUF-5 have the activity of releasing follicle stimulating hormone and the like, but there have been no reports on (1) the activity of stimulating formation of bone, (2) the activity of inhibiting growth of cancer cells or (3) the activity of treating anemia, as in the present invention.

In more detail, BUF-4 and BUF-5 of the present invention may be used for therapy and prophylaxis of human osteoporosis since they may be used to effect calcification, i.e., osteogenetic action on osteoblast-like cell line MC3T3 without exhibiting toxicity to mouse and human culture cells.

Furthermore, the BUF-4 and BUF-5 of the present invention may be used to inhibit the growth of cancer cells without exhibiting toxicity to culture cells of mouse and human. Therefore, BUF-4 and BUF-5 may be used for the safe and effective prophylaxis and treatment of human cancer.

In addition, the BUF-4 and BUF-5 of the present invention may be used for the effective prophylaxis and treatment of anemia caused by reduced production of erythrocytes, and BUF-4 and BUF-5 may be used for the safe and effective prophylaxis and treatment of human anemia.

Therefore, the pharmaceutical compositions of the present invention may be used as drugs for treating osteoporosis, cancer and anemia.

The pharmaceutical compositions of the present invention comprise as the effective ingredient, at least one substance selected from polypeptides BUF-4 and BUF-5. Thus, the pharmaceutical compositions may contain the BUF-4 and BUF-5 singly or may contain them as an admixture of two or more.

The pharmaceutical composition of the present invention is mainly administered parenterally (intravenous, subcutaneous, intramuscular, percutaneous, transmucous).

The dosage of the above-described effective ingredient may be varied depending upon conditions but, when any substance of BUF-4 and BUF-5 is used singly, a daily dose may generally be approximately 0.01 mg to 100 mg for adult in any case. The dose may be administered as a single dose or by dividing into several dosages.

Further when two of BUF-4 and BUF-5 are administered in combination (that is, BUF-4 and BUF-5), a daily dose may generally be also approximately 0.01 mg to 100 mg for adult and may be administered as a single dose or by dividing into several dosages, since the pharmacological effect of each substance is almost identical.

Of course, the dose may vary depending upon conditions and body weight of the patient and other factors acceptable to one skilled in the art and hence, it is unnecessary to strictly follow the dose described above but the dose may be determined depending upon situation.

Medical preparations containing BUF-4 and/or BUF-5, etc. as the effective ingredient(s) which are used in the present invention may be prepared in a conventional manner and are mainly prepared in forms suitable to be administered by injection, such as a solution. In addition, these substances may also be prepared into other preparatory forms such as capsules, tablets, etc. In the case where injections are prepared, the main component(s), BUF-4 and/or BUF-5 may be added with, if necessary, a pH controlling agent, a buffer, a stabilizer, a preservative, etc. and prepared into intravenous, subcutaneous or intramuscular injections. Further where oral preparations are prepared, the main component(s), BUF-4 and/or BUF-5 may be added with a carrier and, if necessary, further a binder, a disintegrator, a coloring agent, etc. and prepared into tablets, capsules, etc.

Next, a method for producing BUF-4 and BUF-5 having an osteogenesis stimulating activity, anemia-treating activity and anticancer activity is briefly described below.

Production of BUF-4 and BUF-5 is carried out by recombinant DNA engineering and hence, only its outline is described below.

To produce BUF-4, eucaryotic cells transformed by a plasmid containing a gene encoding BUF-4, i.e., monomer A and monomer B may be cultured in medium and BUF-4 is produced in the culture solution. To produce BUF-5, eucaryotic cells transformed by a plasmid containing a gene encoding BUF-5, i.e., monomer B may be cultured in medium and BUF-5 is produced in the culture solution (Japanese Patent Application Laid-Open No. 119679/1988).

Now the thus produced BUF-4 or BUF-5 can be purified in a manner similar to conventional polypeptide purification. Crude polypeptide standard can be obtained by, for example, concentrating the culture solution, salting-out polypeptide from the concentrate and then performing ion exchange chromatography using an anionic exchanger. By hydrophobic chromatography or chromatofocusing of the crude standard, almost all protein impurities can be removed. By using both chromatographic means in combination, an enhancement of purification can be obtained. The thus-purified standard product can further be purified by performing high efficiency gel filtration or ion exchange chromatography through reversed phase high performance liquid chromatography (HPLC) or FPLC (manufactured by Pharmacia, Fast Protein Peptide Polynucleotide Liquid Chromatography) system equipped with Super Rose or Mono Q HR5/5 column.

Independently from the conventional polypeptide purification as described above, BUF-4 and BUF-5 may also be purified by a method of purification using organic solvents containing organic acids in a definite concentration which was developed by one of the present inventors. The safety of the pharmaceutical preparation in accordance with the present invention may be established by animal toxicity tests.

The pharmaceutical compositions in accordance with the present invention which comprise BUF-4 and/or BUF-5 as the effective ingredient may be used for drastic treatment of osteoporosis since the composition accelerates calcification, namely, osteogenesis, unlike activated vitamin $D_3$, calcitonin, etc., which are conventional drugs for treating osteoporosis.

Furthermore, the drugs for the treatment of osteoporosis of the present invention may also be advantageously used without causing side effects such as hyper-calcinurea, etc., unlike activated vitamin $D_3$.

Moreover, the pharmaceutical compositions of the present invention may also be used for the effective prophylaxis and therapy of anemia caused by Friend leukemia. Therefore, the drugs for treating anemia of the present invention may be used for treating anemia caused by reduced erythrocytes or hemoglobin which are induced by leukemia, malignant tumors such as multiple myeloma, lymphoma, etc.

In addition, the pharmaceutical compositions of the present invention can also exhibit an excellent anticancer activity with minimal side effects.

Furthermore, BUF-4 and/or BUF-5 are proteins of human origin so that antigenicity is low and allergy may be caused only with difficulty, which allows their use over long periods of time.

Therefore, the pharmaceutical compositions of the present invention are drugs that may be used (1) for treating osteoporosis, (2) as anticancer agents and (3) for treating anemia.

Having generally described this invention, a further understanding can be obtained by reference to certain specific examples which are provided herein for purposes of illustration only and are not intended to be limiting unless otherwise specified.

The effect of BUF-4 and BUF-5 in the accumulation of Ca by osteoblast-like cells may be measured as follows.

EXAMPLES

EXAMPLE 1

The effect of BUF-4 and BUF-5 on the accumulation of Ca by osteoblast-like cells may be measured as follows.

Osteoblast-like cell line MC3T3-El (H. Kodama et al., Jpn. J. Oral Biol., 23, 899–901 (1981)) is suspended in 1 ml of 10% fetal bovine serum-containing α-MEM medium in a concentration of $2 \times 10^5$. The suspension is inoculated on a 24 multi-well plate followed by settling at 37° C. in the presence of 5% $CO_2$. The medium is gently withdrawn 2 days after and 1 ml of the same medium is freshly added thereto. After that, the medium is replaced every 2 days. On day 12, the medium is exchanged for 1 ml of α-MEM medium (containing 1% fetal bovine serum, 20 mM HEPES and 2.9 mM $PO_4^-$) containing $10^{-11}$ to $10^{-9}$M of (a) BUF-4 or (b) BUF-5. Two days after, the medium is again exchanged for 1 ml of the same medium containing 100,000 cpm of 45$CaCl_2$ in Group A and for 1 ml of the same medium containing 1 μCi of [$^3$H]TdR in Group B. After settling for 2 days at 37° in the presence of 5% $CO_2$, the system is washed twice with phosphate buffer saline. Subsequently, the cells in Group A are transferred to a vial for liquid scintillation counter and 0.1 ml of 60% $HClO_4$ and 0.2 ml of 30% of $H_2O_2$ are added to the cells. After heating at 70° C. for an hour, methyl cellosolve is added to the cells and the radioactivity is counted. In Group B, 10% TCA is added to the cells. After washing again twice and then with ethanol-ether (3:1), the system is dissolved in 250 μl of NaOH and the radioactivity is counted. In any case, the systems to which BUF-4 and BUF-5 are not added are controls, respectively.

Accumulation of $^{45}$Ca on the substrate phase by MC3T3-E1 cells dose-dependently increases by the action of BUF-4 and BUF-5. Furthermore, intake of [$^3$H] thymidine into DNA decreases by the action of BUF-4 and BUF-5.

EXAMPLE 2

The inhibition of cancer cell growth by BUF-4 and BUF-5 may be assessed as follows.

A medium used for subculturing respective cancer cells is used as medium. That is, Ham's F12 medium is used for mouse Friend leukemia cells F5-5, RPMI-1640 medium (Rosewell Park Memorial Institute 1640 medium) is used for K562 and THP-1 cells, and Dulbecco's modified Eagle medium is used for the other cells. To each medium, 10% fetal bovine serum (hereafter simply referred to as FBS) is added.

Firstly, each of the media described above which contain 0.63% agar is inoculated onto a 96 well plate as a supporting layer in a concentration of 50 μl/well. The respective cells are suspended in the 0.3% agar-containing media, respectively and the resulting suspension are inoculated in a concentration of 50 μl/well. In this case, mouse Friend leukemia cells, K562 cells and THP-1 cells are inoculated in a density of 100 counts/well; A549 and KB cells in a density of 200 counts/well and other cells in a density of 300 counts/well, in each well. Next, serially diluted BUF-4 sample is added in a concentration of 100 μl/well. After culturing for 10 to 20 days at 37° C. in the presence of 5% carbon dioxide gas and 95% air, the number of colonies in which the diameter is larger than 50 μm is counted.

Incubation of mouse Friend leukemia cells in soft agar semi-solid medium results in the formation of colonies. Using the colony formation as an index, influence of BUF-4 on cell growth is examined, whereby dose-dependent growth inhibition is noted.

Likewise influence of BUF-5 on cell growth is examined; dose-dependent growth inhibition is noted almost similarly to the case of BUF-4.

EXAMPLE 3

The activities of BUF-4 and BUF-5 against human cancer cells may also be examined.

BUF-4 inhibits colony formation of myelogenous leukemia cell K-562, myelogenous leukemia cell THP-1, mammary cancer MCF-7, lung cancer cell A-549, etc. in soft agar semi-solid medium.

BUF-5 also inhibits growth of the cancer cells described above as in BUF-4.

EXAMPLE 4

The antianemia effect of BUF-4 and BUF-5 may be measured as follows.

ddY mice (male, age of 5 weeks, Tokyo Experimental Animal Co., Ltd.) are used as test animals, one group being 5 mice. In the ascites of mice, subcultured mouse Friend leukemia cells F5-5 are intraperitoneally transplanted in $2 \times 10^6$ each.

BUF-4 (freeze dried standard product) is dissolved in sterilized physiological saline to prepare 5000 U/ml of a drug for injection. The injection described above is intraperitoneally and intravenously administered to the BUF-4-administered group in a dose of 0.2 ml (1000 U) for 3 consecutive days after the day following the transplantation of F5-5 cells. On days 14 and 21 after the transplantation of F5-5 cells, blood is collected in a hematocrit tube through the tail vein. By centrifuging at 12,000 r.p.m. for 5 minutes, the hematocrit level is determined in a conventional manner. For the control group, physiological saline is administered. In the groups to which BUF-4 is administered intraperitoneally and intravenously, an increase in the hematocrit level is noted as compared to the control group. BUF-5 also shows a similar effect. Safety of BUF-4 and BUF-5 is established.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of treating anemia, comprising administering an antianemia effective amount of BUF-5 to a patient in need thereof.

* * * * *